(12) United States Patent
Priebe

(10) Patent No.: US 6,406,680 B1
(45) Date of Patent: Jun. 18, 2002

(54) X-RAY CONTRAST AGENTS

(75) Inventor: Hanno Priebe, Oslo (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/655,671

(22) Filed: Sep. 6, 2000

(30) Foreign Application Priority Data

Sep. 17, 1999 (NO) .......................................... 1999 4499
Jul. 21, 2000 (NO) .......................................... 2000 3744

(51) Int. Cl.[7] .............................................. A61K 49/04
(52) U.S. Cl. ...................... 424/9.4; 570/189; 568/671; 568/672; 568/673; 568/674; 568/675; 568/681; 568/686
(58) Field of Search .................. 554/70; 424/9.455, 424/9.4; 568/671, 672, 673, 674, 675, 681, 686; 570/18

(56) References Cited

U.S. PATENT DOCUMENTS

| | | |
|---|---|---|
| 3,342,582 A | 9/1967 | Iserson et al. |
| 3,376,315 A | 4/1968 | Burger et al. ............. 260/340.9 |
| 5,695,742 A | * 12/1997 | Felder et al. ............. 424/9.455 |

FOREIGN PATENT DOCUMENTS

| | | | |
|---|---|---|---|
| DE | 2241155 | 3/1974 | |
| DE | 3142654 A1 | * 5/1983 | |
| DE | 3 142 654 | 5/1983 | |
| EP | 0 316 058 B1 | 5/1992 | |
| JP | 57-102849 | 6/1982 | |
| NO | 153966 | * 6/1986 | ........... C07C/69/62 |

OTHER PUBLICATIONS

Synthesis and Antifungal activity of Trihaloallyl and trihaloacryl Derivatives, Kiyoshi Konishi et al, Holzforschung, vol. 38 1984, pp 225–231.*

Morisawa, K., et al. "Synthesis and Antifungal Activity of Trihaloallyl and Trihaloacryl Derivatives" Holzforschung, vol. 38, 1984, pp. 225–231.

* cited by examiner

*Primary Examiner*—Deborah Carr
(74) *Attorney, Agent, or Firm*—Royal N. Ronning, Jr.; Robert F. Chisholm; Stephen G. Ryan

(57) ABSTRACT

This invention describes a new type of X-ray contrast agents. It has been found that iodinated alkenes containing one or several C=C double bonds substituted with electronic neutral substituents and iodine can be used as X-ray contrast agents. Also new iodoalkene compounds are described.

9 Claims, 8 Drawing Sheets

STRUCTURES AND SYNTHETIC ROUTES TO
IODOALKENES 2, 3, 5 AND 6

IOHEXOL

IODIDE RELEASE FROM AN IODOALKENE WITH AN ELECTRON WITHDRAWING SUBSTITUENT, Nu = NUCLEOPHILE

IODIDE RELEASE FROM AN IODOALKENE WITH AN ELECTRON
DONOR SUBSTITUENT, E+ = ELECTROPHILE, Nu = NUCLEOPHILE

X-RAY ABSORBER GROUP, COUPLING AND HYDROPHILLIC GROUP IN TRIIODOBENZENE- AND IODOALKENE-DERIVATIVES

STRUCTURES AND SYNTHETIC ROUTES TO
IODOALKENES 2, 3, 5 AND 6

STRUCTURES AND SYNTHETIC ROUTES TO
IODOALKENES 9, 12, 13 AND 14

STRUCTURES AND SYNTHETIC ROUTES TO
IODOALKENES 16 AND 18

X-RAY CONTRAST AGENTS

BACKGROUND OF INVENTION

This invention describes a new type of X-ray contrast agents including their formulation and use. It has been found that iodinated alkenes could be used as X-ray contrast agents like the traditional iodinated aromatic contrast agents. The invention covers new iodinated alkenes, their use as X-ray contrast agents, as well as the use of known iodoalkenes as X-ray contrast agents.

Many of today's X-ray contrast agents are based on triiodinated aromatics. The product iohexol (Omnipaque®) by Nycomed Imaging AS, given in FIG. 1, is an example of such a triiodinated aromatic.

There is a continuous need for new X-ray contrast agents, especially compounds with more simple structures than the traditional iodinated aromatic compounds. Such compounds can be prepared with fewer and easier synthetic steps than necessary for the preparation of triiodinated aromatic X-ray contrast agents.

It has previously been investigated whether certain iodinated alkenes may be used as X-ray contrast agents. H. Suter & H. Zutter describe in Pharm. Acta Helv. 50, 151–152, 1975, How fumaric acid derivatives were tested as potential X-ray contrast agents. Several fumaric acid derivatives were synthesised with different substituents that should give high aqueous solubility. One of those was diiodofumaric acid bis-[di-ethanol-amide]. The toxicity (LD 50 in mice, intravenous) was found to be less than 1 g/kg for all substances. The corresponding value for iohexol is 33.7 g/kg. The reason for this high toxicity is probably that the diiodofumaric acid structures are equivalent to a "vinylogeous acid-iodide" that can release iodide by an addition-elimination reaction with nucleophiles, see FIG. 2.

Fumaric acid derivatives and other iodoalkenes with electron withdrawing substituents will probably be unsuitable as X-ray contrast agents. The reason is that such compounds are able to release toxic iodide by an addition-elimination reaction with nucleophiles. In the development of new X-ray contrast agents it is generally desired that the contrast agent shall effect different biological mechanisms in the body as little as possible, because this generally results in lower toxicity and less negative clinical effects. Compounds that can release iodide in reactions with nucleophiles or electrophiles may cause toxic and negative biological effects and should not be used as contrast agents.

Iodoalkenes with electron-donor substituents may add electrophiles in the same way as enamines, see FIG. 3. This is undesirable too since the ammonium group can be cleaved hydrolytically. In addition the iodine is now bound to an $sp^3$ hybridized on which is characteristic for alkylating agent again attack of nucleophiles will release iodide.

Partly as a result of the negative results from the investigation of fumaric acid derivatives it has been generally accepted that only iodinated aromatic compounds can be used as X-ray contrast agents. Other types of highly iodinated compounds that meet the property requirements for X-ray contrast agents like aqueous solubility, non-toxicity and stability have until now not been found.

SUMMARY OF THE INVENTION

It has now, surprisingly, been found that it is possible to use iodinated alkenes as X-ray contrast agents equivalent to iodinated aromatic contrast agents. Different from the compounds described by Suter and Zutter the iodinated alkenes in the present invention are characterized by that they neither contain electron withdrawing nor electron donating substituents at the C=C double bond. As a consequence there are no problems caused by addition of electrophiles or nucleophiles followed by loss of iodide, while the utility as an X-ray contrasr agent is maintained.

DETAILED DESCRIPTION OF THE INVENTION

Figure 1:
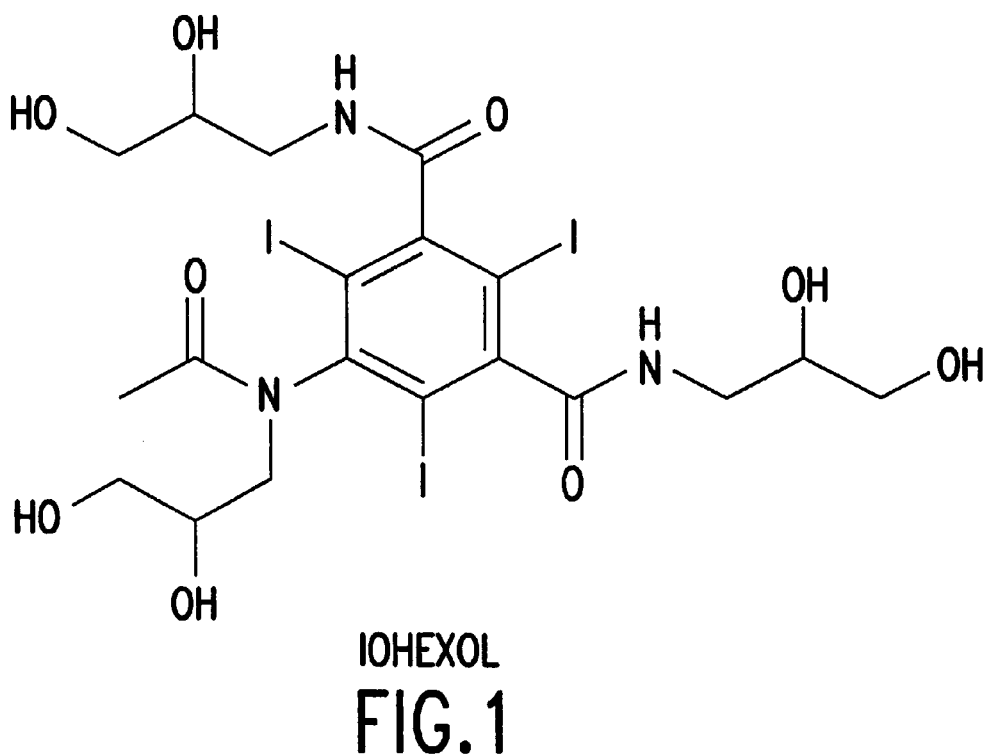
FIG. 1 presents the structure of Iohexol.
Figure 2:
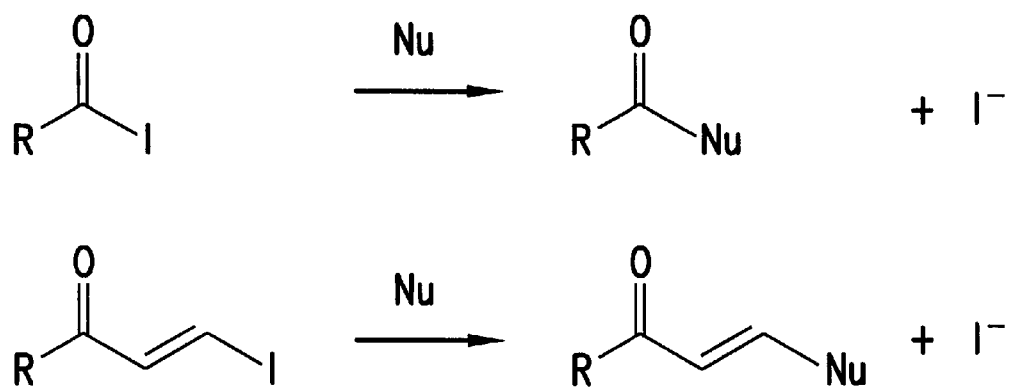
FIG. 2 presents iodide release mechanisms of iodoalkenes with an electron withdrawing substituent in the presence of a nucleophilic species.
Figure 3:
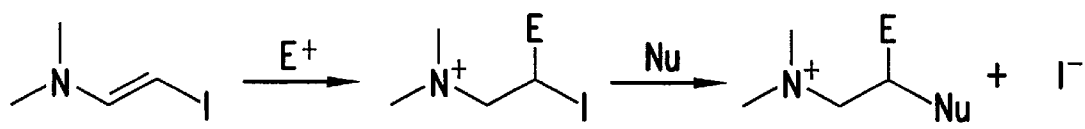
FIG. 3 presents iodide release mechanisms of iodoalkenes with an electron donor substituent in the presence of a nucleophilic species.
Figure 4:
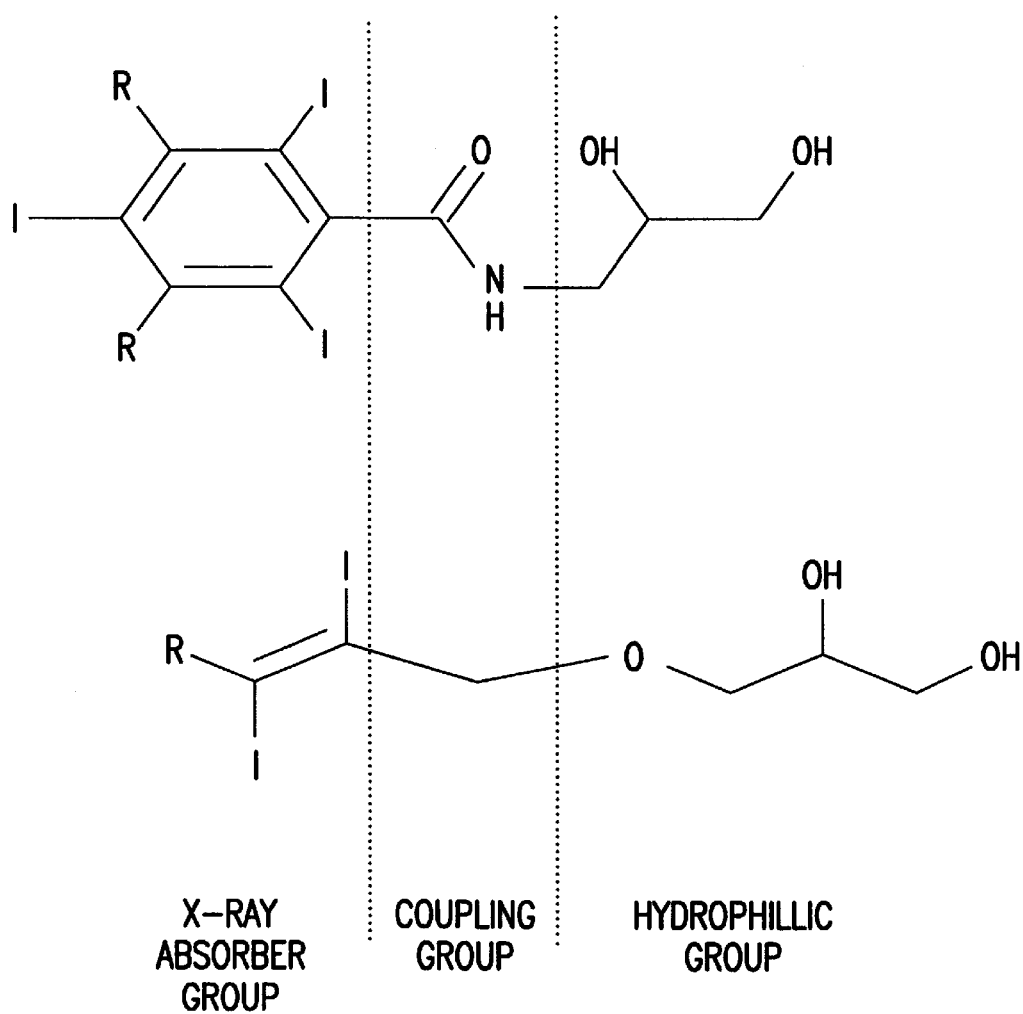
FIG. 4 presents a comparative view of the structures of an iodoalkene and a triodobenzene derivative.

A comparison of the structures of a triiodobenzene derivative and an iodoalkene is given in FIG. 4. In FIG. 4 we distinguish between X-ray absorber group, coupling group and hydrophillic group. In order to mark each group the molecules are divided by two dotted lines.

Compared with triiodobenzene derivatives some of the iodoalkene compounds described in this invention introduce something new in all three subgroups. The iodoalkene compounds have iodoalkene as X-ray absorber group, methylene as coupling group and a hydrophillic group containing both ether and hydroxyl groups. The present invention therefore addresses the use of iodoalkenes as X-ray contrast agents. X-ray contrast agents in accordance with the invention are characterized by electronic neutral substituents at the iodinated C=C doublebond(s), meaning that the substituents do not have an electron donor or electron withdrawing effect. Electronic neutral substituents are called C-substituents or C-groups in contrast to electron donanting X-substituents or electron withdrawing Z-substituents. (Ian Fleming: Grenzorbitale und Reaktionen organischer Verbindungen, p. 57, Verlag Chemie 1979). The donor/acceptor properties of substituents can be described by Hammet substituent constants $\sigma_m$ og $\sigma_p$, resonance effect parameter R and field/inductive effect parameter F (C. Hansch, A. Leo and R. W. Taft, Chem. Rev. 1991, 91, 165–195). The electron donor/acceptor effect of substituents acting through space is called field effect, whereas the effect acting through σ-bonds is called inductive effect. The electron donor/acceptor effect of substituents on double bonds or aromatic rings originating from the subtituents π- or non-bonding n-electrones is called resonance effect.

Compounds for use as X-ray contrast agents can further be described by the following formula A:

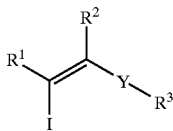

A where:
  Y=(IC=CI)$_{0-1}$ and the groups R$^1$ and R$^2$ are iodine or a C-group, and R$^3$ is a C-group. C-group means here a group that is electronically neutral. It is preferred that the C-groups R$^1$, R$^2$ and R$^3$ different from iodine have the following area for resonance effect R and field effect F: 0.06≧R≧−0.45 and 0.24≧F≧−0.03.
  More preferred is the range 0.04≧R≧−0.39 and 0.22≧F≧−0.02.
  Most preferred is the range 0.02≧R≧−0.33 and 0.20≧F≧−0.01.
  FIG. 8 in appendix 1 shows a plot of the resonance effect parameter R and the field /inductive effect parameter F for different substituents. Strong field/inductive acceptors like NO$_2$ (F=0.65) have high positive F-values. Strong resonance donors like NMe$_2$ (R=−0.98) have high negative R-values. The preferred electronic neutral substituents are located in the neighbourhood of CH$_2$OMe (F=0.13 and R=−0.12).
  R$^1$, R$^2$ and R$^3$ can further be equal or different.
  It is further preferred that the compounds contain at least 2 iodine atoms. An increase of the number of iodine atoms will give increased contrast effect.
  The electronic neutral C-groups are preferably hydrophyllic groups that constitute to the aqueous solubility of the contrast agent. The aqueous solubility increases with increasing number of hydrophillic groups. Hydroxylated alkyl chains are examples of hydrophillic C-substituents.
  The number of iodine atoms and the number of hydrophillic groups must be balanced in order to obtain the desired contrast effect and sufficient aqueous solubility.
  Preferred are compounds with formula A for use as X-ray contrast agent, wherein
    Y=(IC=CI)$_{0-1}$
    R$^1$=H, I, CH$_2$OH, R$^3$
    R$^2$=H, I, CH$_2$OH, R$^3$
    R$^3$=H, CH$_2$—R$^4$, CH$_2$—R$^5$, CH(R$^4$)$_2$, CHR$^4$R$^5$, CR$^4$(R$^5$)$_2$, R$^5$, (CH$_2$)$_{1-3}$—CO—NR$^5$R$^6$
    R$^4$=O—R$^5$, O—(CH$_2$CH$_2$—O)$_{1-7}$—R$^6$, NH—CO—R$^6$, NH—CO—O—(CH$_2$CH$_2$—O)$_{1-6}$—R$^6$, NH—CO—O—R$^6$, NH—CO—NH$_2$, O—CO—R$^6$, O—CO—O—R$^6$, O—CO—N—R$^6$, O—CO—NH—R$^6$
    R$^5$=H, C$_{1-8}$ alkyl chain which is unbranched or branched and which is substituted with one or several OH-groups.
    R$^6$=H, C$_{1-7}$ alkyl chain, R$^5$.
  More preferred are compounds with formula A for use as X-ray contrast agent, wherein
    Y=(IC=CI)$_{0-1}$
    R$^1$=H, I, CH$_2$OH, R$^3$
    R$^2$=H, I, CH$_2$OH, R$^3$
    R$^3$=H, CH$_2$—R$^4$, CH$_2$—R$^5$, CH(R$^4$)$_2$, CHR$^4$R$^5$, R$^5$
    R$^4$=O—R$^5$, O—(CH$_2$CH$_2$—O)$_{1-7}$—R$^6$, NH—CO—R$^6$, NH—CO—O—R$^6$, O—CO—R$^6$, O—CO—NH—R$^6$
    R$^5$=H, C$_{1-7}$ alkyl chain which is unbranched or branched and which is substituted with one or several OH-groups.
    R$^6$=H, C$_{1-6}$ alkyl chain, R$^5$.
  Most preferred are compounds with formula A for use as X-ray contrast agent, wherein
    Y=(IC=CI)$_{0-1}$
    R$^1$=H, I, CH$_2$OH, R$^3$
    R$^2$=H, I, CH$_2$OH, R$^3$
    R$^3$=CH$_2$—R$^4$, CH$_2$—R$^5$
    R$^4$=O—R$^5$, O—(CH$_2$CH$_2$—O)$_{1-6}$—R$^6$, O—CO—R$^6$, O—CO—NH—R$^6$
    R$^5$=H, C$_{1-6}$ alkyl chain which is unbranched or branched and which is substituted with one or several OH-groups.
    R$^6$=H, C$_{1-5}$ alkyl chain, R$^5$.
  Especially preferred are the compounds 13, 14 and 18 shown in FIG. 6 and in example 10, 11 and 14 respectively.
  The groups named above can be defined as C-groups and they have neither electron donor nor electron acceptor properties, and thus vil be located within a limited area in FIG. 8, appendix 1.
  Another aspect of the invention are compounds that release or decompose to active X-ray contrast agents of structure type A as previously defined.
  A further aspect of this invention is new iodinated alkenes. These chemical compounds can also be described by structure A where Y=(IC=CI)$_{0-1}$ and the groups R$^1$ and R$^2$ are iodine or electronic neutral C-groups and R$^3$ is an electronic neutral C-group. The compounds are further characterized by
    Y=(IC=CI)$_{0-1}$
    R$^1$=H, I, CH$_2$OH, R$^3$
    R$^2$=H, I, R$^3$
    R$^3$=CH$_2$—R$^4$, CH$_2$—R$^5$, CH(R$^4$)$_2$, CHR$^4$R$^5$, CR$^4$(R$^5$)$_2$, R$^5$
    R$^4$=O—R$^5$, O—(CH$_2$CH$_2$—O)$_{2-7}$—R$^6$, NH—CO—R$^6$, NH—CO—O—(CH$_2$CH$_2$—O)$_{1-6}$—R$^6$, NH—CO—O—R$^6$, NH—CO—NH$_2$ $_R{}^5$=C$_{3-8}$ alkyl chain which is unbranched or branched and which is substituted with one or several OH-groups.
    R$^6$=H, C$_{2-7}$ alkyl chain, R$^5$
  Preferred are compounds of formula A where
    Y=(IC=CI)$_{0-1}$
    R$^1$=H, I, CH$_2$OH, R$^3$
    R$^2$=H, I, R$^3$
    R$^3$=CH$_2$—R$^4$, CH$_2$—R$^5$, CH(R$^4$)$_2$, CHR$^4$R$^5$, R$^5$
    R$^4$=O—R$^5$, O—(CH$_2$CH$_2$—O)$_{2-7}$—R$^6$, NH—CO—R$^6$, NH—CO—O—R$^6$
    R$^5$=C$_{3-7}$ alkyl chain which is unbranched or branched and which is substituted with one or several OH-groups.
    R$^6$=H, C$_{2-6}$ alkyl chain, R$^5$.
  More preferred are compounds of formula A where
    Y=(IC=CI)$_{0-1}$
    R$^1$=H, I, CH$_2$OH, R$^3$
    R$^2$=H, I, R$^3$
    R$^3$=CH$_2$—R$^4$, CH$_2$—R$^5$
    R$^4$=O—R$^5$, O—(CH$_2$CH$_2$—O)$_{2-7}$—R$^6$
    R$^5$=C$_{3-6}$ alkyl chain which is unbranched or branched and which is substituted with one or several OH-groups.
    R$^6$=H, C$_{2-5}$ alkyl chain, R$^5$.
  Especially preferred are the compounds 13, 14 and 18 shown in FIGS. 6 and 7 and in example 10, 11 and 14 respectively.
  It has now surprisingly been found that the synthetic path for the preparation of iodoalkenes of structure A is very simple with few steps relative to the syntesis of conventional aromatic X-ray contrast agents. Possible important advantages of these syntheses are e.g. reduction of equipment, process time and costs relative to the synthesis of conventional aromatic X-ray contrast agents.

Figure 5:
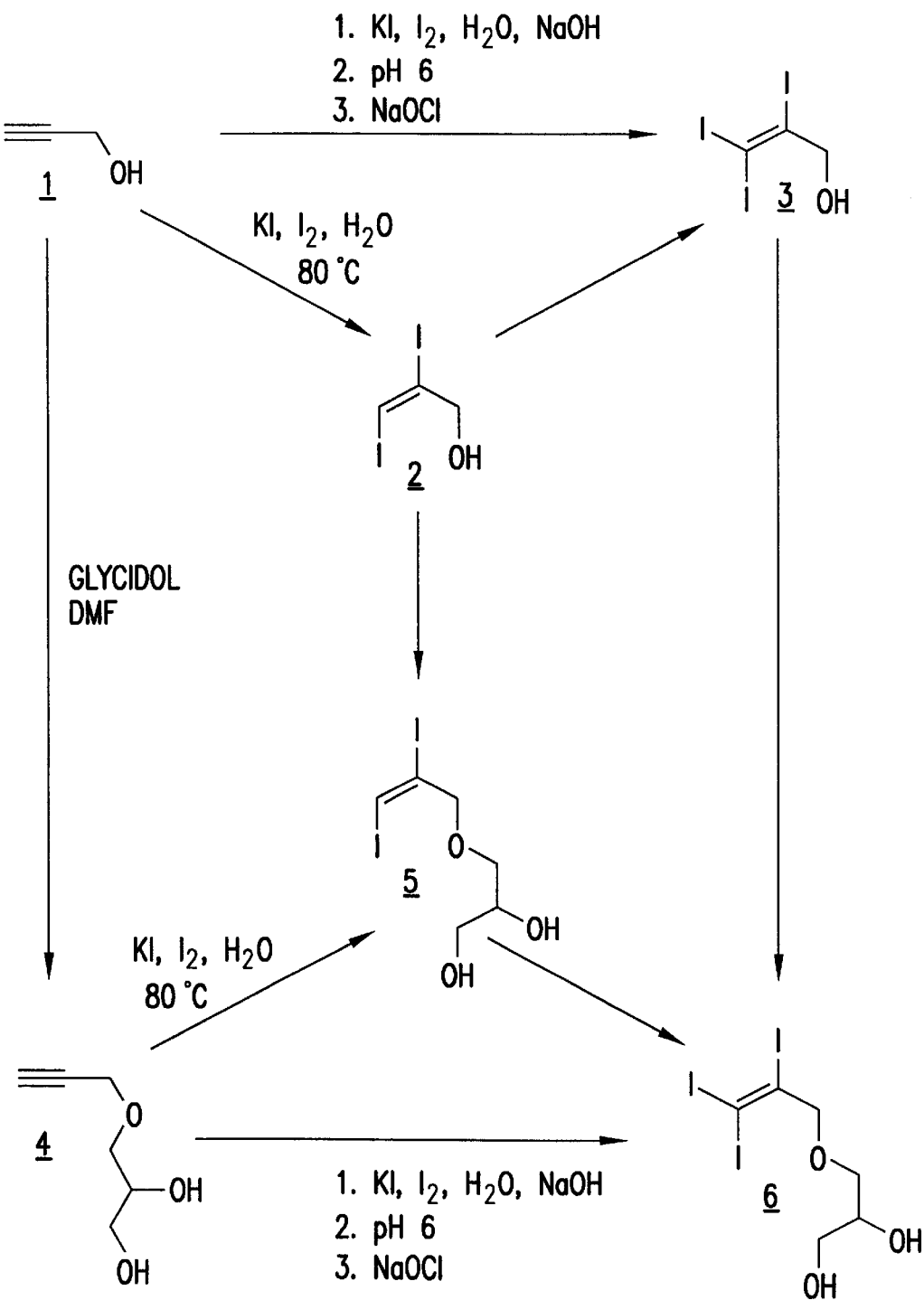
FIG. 5 presents the structure and synthetic pathways for the compounds described in Examples 1, 2, 4, and 5.
Figure 6:
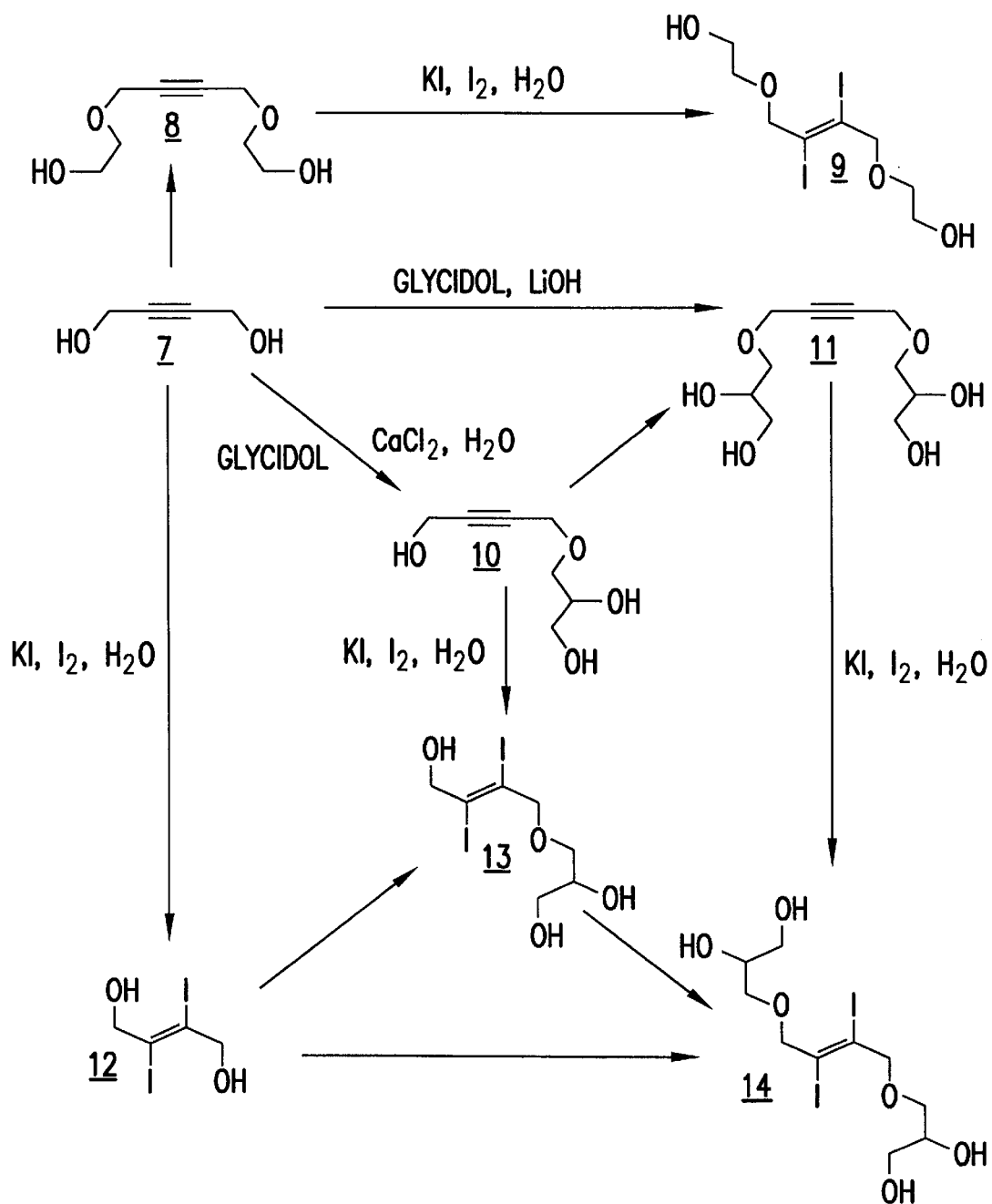
FIG. 6 presents the structure and synthetic pathways for the compounds described in Examples 6, 9, 10, and 11.
Figure 7:
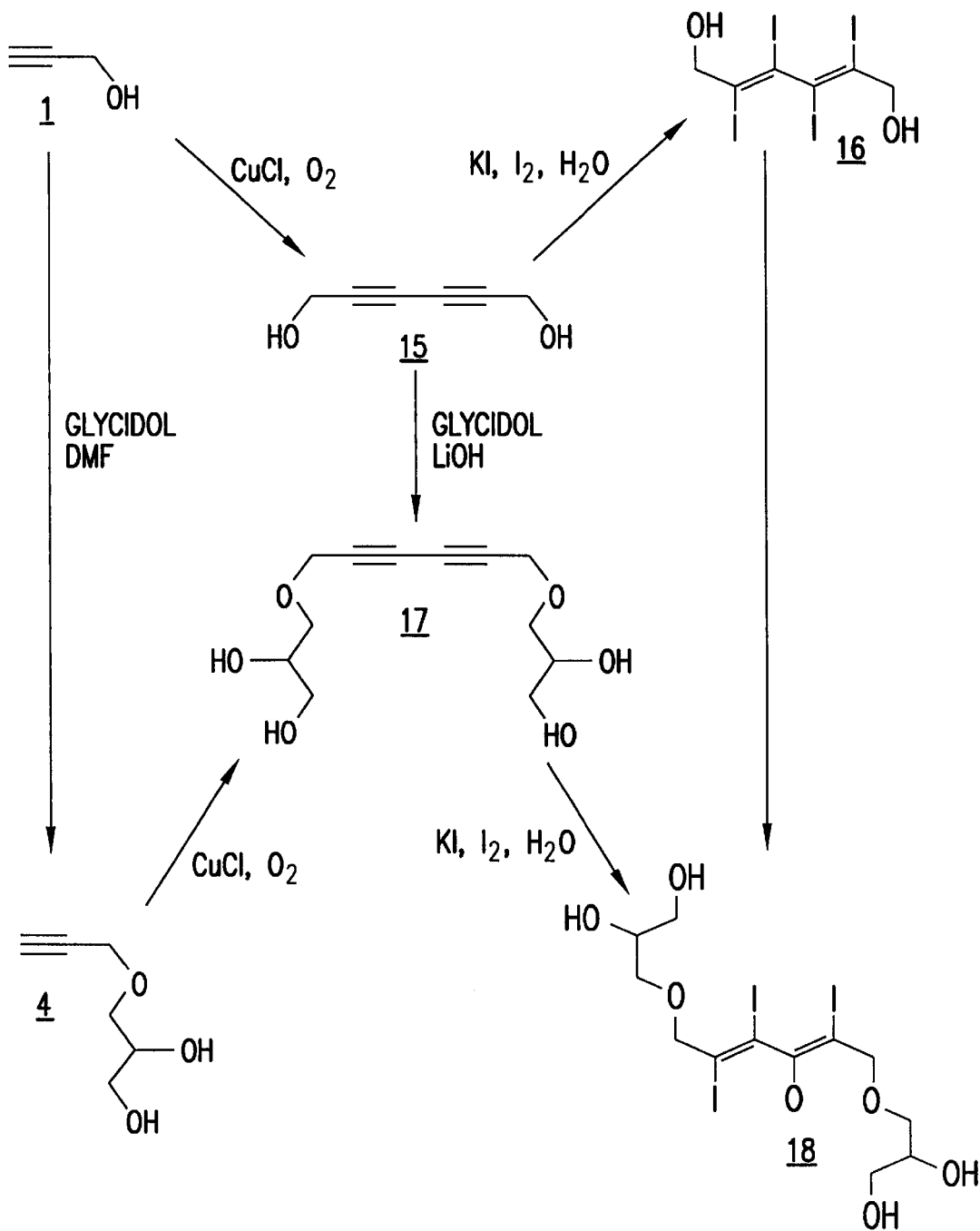
FIG. 7 presents the structure and synthetic pathways for the compounds described in Examples 12 and 14.
Figure 8:
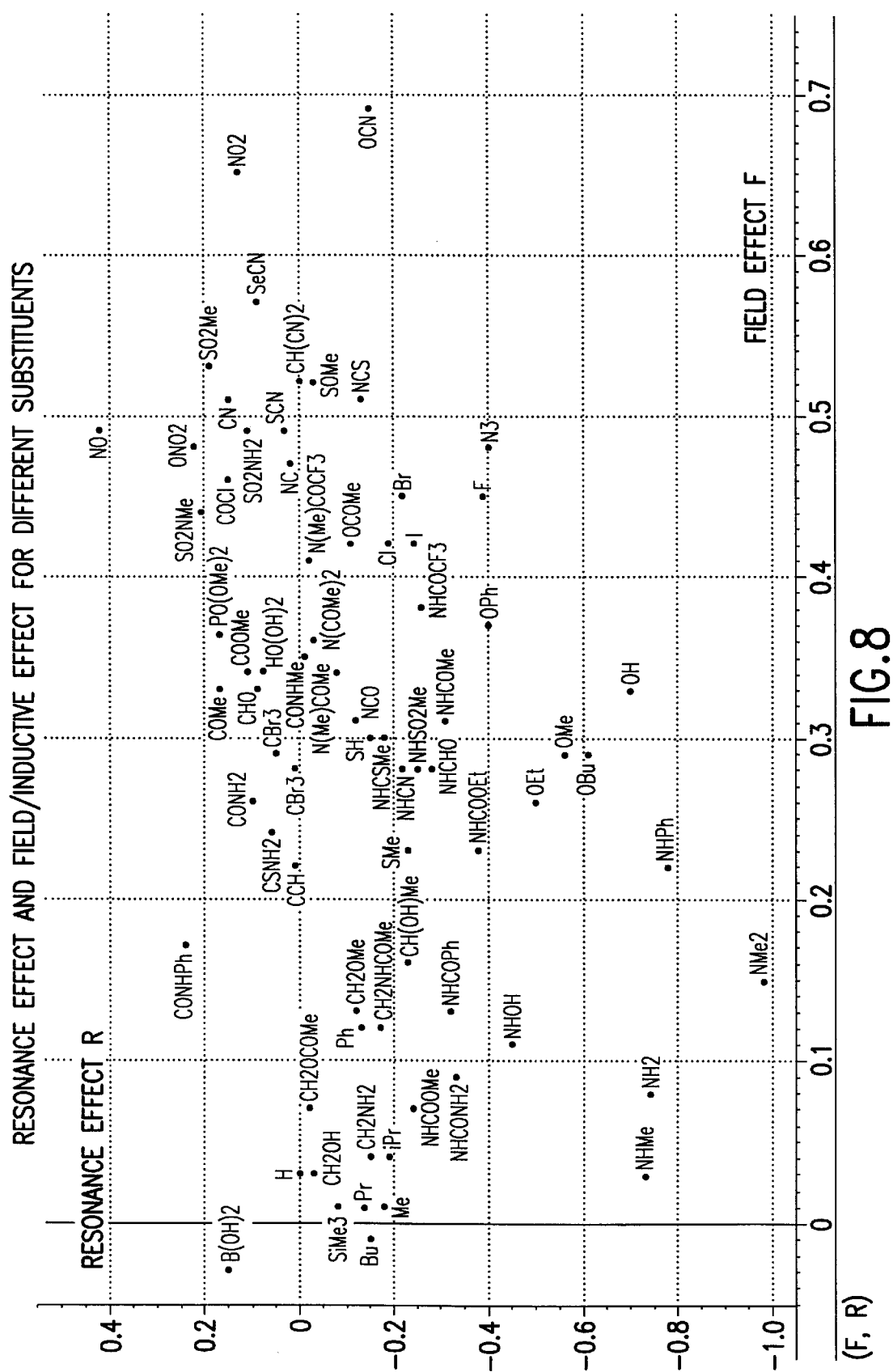
FIG. 8 graphically depicts the field effect vs. resonance effect for a number of different substituents.

Possible synthetic routes to iodoalkenes according to this invention are summarized in FIGS. 5, 6 and 7. The iodoalkenes were preferred prepared by iodination of substituted alkynes, as e.g. the synthesis of compond 6 from compound 4 shown in FIG. 5. The hydrophilic groups may alternatively be bound to iodoalkenes in the last step, see e.g. the synthesis of compound 6 from compound 3.

The present invention therefor also includes a process for the preparation of iodinated alkenes with formula A by using the synthetic routes given in FIGS. 5, 6 and 7. The iodination steps are described in examples 4, 5, 6, 10, 11 and 14. The iodination of alkynes is done in water as a cheap and environmental friendly solvent.

The present invention also includes new processes for the preparation of hydrophillic alkynes as precursors to iodoalkenes with structure A. The preparation of compounds 4, 10, 11 and 17 is shown in FIGS. 5, 6 and 7 and is described in examples 3, 7, 8 and 13 respectively. The hydrophillic alkynes 4, 10 and 11 and other equivalent alkynes were prepared by an O-alkylation of alkynols with glycidol or glycidol analogues.

The invention also includes the use of compounds given by structure A as X-ray contrast agent. The compounds may be formulated with conventional carriers and solvents, e.g. water, in order to produce a diagnostic X-ray contrast agent.

Seen from another aspect the invention therefor gives a diagnostic composition consisting of a compound of structure A (as defined above) together with at least one physiological acceptable carrier or solvent, e.g. in aqueous solution for injection, eventually with added plasma ions or dissolved oxygen. For use as an X-ray contrast agent it is advantageous to treat the compounds according to the invention by sterile filtration instead of autoclavation. X-ray contrast agents according to the inventions can be produced in "ready for use" concentrations or can be formulated in concentrated form for dilution prior to administration. Compositions in "ready for use" form will typically have iodine concentrations of at least 100 mgI/ml, preferred at least 150 mgI/ml and most preferred at least 300 mgI/ml. Effective ion concentrations can be obtained with isotonic solutions, and it may be desirable to obtain an isotonic solution by addition of plasma ions. Examples of possible plasma ions are ions of sodium, calcium, potassium and magnesium. Plasma ions can be present as counter ions in ionic contrast agents or they can be present in form of salts with physiologically acceptable counter ions, e.g. chloride, sulfate, phosphate, hydrogen carbonate and so on. In addition to plasma cations the X-ray contrast agent may rise other counter ions e.g. alkaline and alka earth metal ions, ammonium, meglumine, ethanolamine, diethanolamine, chloride, phosphate and hydrogen carbonate. Other counter ions conventionally used in pharmaceutical formulations may also be used. The formulation may in addition also contain in other components used in pharmaceutical formulations, e.g. buffers.

Seen under another aspect the invention gives a method to generate an X-ray image of a human beeing or an animal, preferrably a human beeing, wherein the method is characterized by administration of a contrast agent according to the invention and generation of an X-ray image.

The following mono-, di-, tri- and tetraiodinated model compounds are examples of compounds that can be used as X-ray contrast agents according to this invention, some as water-soluble- and others as non-water soluble agents. Water-soluble agents are preferred.

2-Iodo-2-propene-1-ol
3-Iodo-2-propene-1ol, E- and/or Z- isomer
3-(2-Iodo-2-propenyloxy)-propane-1,2-diol
2-Iodo-2-butene-1,4-diol, E- and/or Z- isomer
2-[(2,3-Diiodo-4-hydroxy-2-butenyl)oxy]-ethanol
2 2,3-Diiodo-2-propene-1-ol
3 2,3,3-Triiodo-2-propene-1-ol
5 3-(2,3-Diiodo-2-propenyloxy)-propane-1,2-diol
6 3-(2,3,3-Triiodo-2-propenyloxy)-propane-1,2-diol
9 2,2'-[2,3-Diiodo-2-butene-1,4-diylbis(oxy)]-bis-ethanol
12 2,3-Diiodo-2-butene-1,4-diol
13 3-[(2,3-Diiodo-4-hydroxy-2-butenyl)oxy]-propane-1,2-diol
14 3,3'-[2,3-Diiodo-2-butene-1,4-diylbis(oxy)]-bis-propane-1,2-diol
16 2,3,4,5-Tetraiodo-2,4-hexadiene-1,6-diol
18 3-[6-(2,3-Dihydroxy-propoxy)-2,3,4,5-tetraiodo-hexa-2,4-dienyloxy]-propane-1,2-diol According to the invention the following alkyne compounds can be used as precursors to iodoalkenes:
4 3-(2-Propynyloxy)-propane-1,2-diol
8 1,4-Bis-(2-hydroxyethoxy)-2-butyne
10 3-[(4-Hydroxy-2-butynyl)oxy]-propane-1,2-diol
11 3,3'-[2-Butyne-1,4-diylbis(oxy)]-bis-propane-1,2-diol
17 3-[6-(2,3-Dihydroxy-propoxy)-hexa-2,4-diynyloxy]-propane-1,2-diol According to the invention the following compounds can be used as catalysts under O-alkylation reactions of alkynols with glycidol or glycidol equivalents:
$SOCl_2$, $H_2SO_4$, DMF, $CaCl_2$ and/or $CaCl_2*2H_2O$, $Na_2HPO_4$, $K_3PO_4$, 2,6-Dimethyl-pyridine, LiOH, NaOH, $Ca(OH)_2$, $NaOAc*3H_2O$.

According to the invention the following compounds can be used as glycidol equivalents under O-alkylation reactions together with equimolar amounts of base, e.g. NaOH, KOH, $Ca(OH)_2$:
3-Halo-propane-1,2-diol where halo=Cl, Br, I
2-Halo-propane-1,3-diol where halo=Cl, Br, I The aqueous solubilities (g/L) of some compounds according to this invention are given in table 1.

TABLE 1

Aqueous solubilities of iodinated alkenes according to this invention

| Compound | Aqueous solubility at 20° C. (g/L) | iodine content (%) |
|---|---|---|
| 2 | 0.391 | 82 |
| 3 | 0.198 | 87 |
| 5 | 18.38 | 66 |
| 6 | 0.5 | 75 |
| 9 | 7.2 | 59 |
| 12 | 0.534 | 75 |
| 13 | >1200 | 61 |
| 14 | >1200 | 52 |
| 16 | 0.183 | 82 |
| Iohexol | >1200 | 46 |

EXAMPLES

The invention vil further be illustrated with reference to the following examples, which are intended to be illustrative of certain embodiments of the present invention, but are not intended to be illustrative of all embodiments.

Example 1

2,3-diiodo-2-propene-1-ol (2); [71264-49-8]

2 was synthesized from propargyl alcohol 1 as described by Iserson, H., Smith, H. Q., U.S. Pat. No. 3,342,582, Sep.

19, 1967. The crude product was recrystallised from water and gave 2 in 52% yield. MP. 52–52.5° C. (lit. 51.5–52.5). TLC on silica; EtAc:CH$_3$CN=1:1; R$_f$=0.69. Aqueous solubility at 20° C.=3.913 g/L.

Spectroskopic Data

MS [m/z, (% rel. int.), fragment]: 310.2 (63) M, 254.1 (10)I$_2$, 183.1 (100) M-I, 127.0 (21) I, 56.1 (7) M-2I, 55.1 (40) M-(2I+H). IR [$\square^{KBr}$, cm$^{-1}$]: 4268 (w), 3690 (w), 3251 (s, broad, O—H), 3058 (s, =C—H), 2949 (m, C—H), 2912 (m, C—H), 2839 (m, C—H), 2694 (m), 2426 (w), 2081 (w), 1710 (w), 1563 (m, C=C), 1435 (s, CH$_2$), 1353 (m, CO—H), 1242 (m, CH$_2$+CO—H), 1218 (s, CO—H), 1074 (m, C—OH), 1051 (s, C—OH), 1018 (m, C—OH), 1009 (s, C—OH), 958 (s, C—OH), 783 (s, =C—H), 633 (s, =C—H), 586 (m), 531 (s). $^1$H-NMR [300 MHz, CDCl$_{35}$, 2.56 (1H, s, OH), 4.29 (2H, d, J=0.92 Hz, , 7.05 (1H, t, $^4$J$_{HH}$=0.9 Hz, =CH—) ppm. $^{13}$C-NMR [300 MHz, CDCl$_3$]: $\square$70.62, 79.91, 104.10 ppm. UV [MeOH]: $\square_{max}$=238.4 nm.

Example 2

2,3,3-triiodo-2-propene-1-ol (3); [42778-72-3]

3 was synthesized from propargyl alcohol 1 as described by Gerhardt, W., Hase, C., DE Pat. No. 3,142,654, Oct. 28, 1981. The crude product was recrystallized from H$_2$O:EtOH=1:1 and gave 3 in 81% yield. MP. 153.5–154.0° C. (lit.: 145–148° C.). TLC on silica; EtAc, R$_f$=0.65. Aqueous solubility at 20° C.=0.198 g/L.

Spectroskopic Data

MS [m/z, (% rel. int.), fragment]: 435.8 (100) M, 308.9 (91) M-I, 253.9 (18) I$_2$, 182.0 (21) M-2I, 127.0 (56) I, 55.0 (27) M-3I, 54 (11) M-(3I+H). IR [$\square^{KBr}$, cm$^{-1}$]: 3193 (s, broad, O—H), 2938 (m, C—H), 2920 (m, C—H), 2861 (m, C—H), 2813 (m, C—H), 2625 (w), 2434 (w), 1548 (m, C=C), 1445 (m, CH$_2$), 1410 (m, CH$_2$), 1345 (w, CO—H), 1220 (m, CO—H), 1051 (s, C—OH), 1024 (s, C—OH), 964 (s, C—OH), 764 (m), 736 (m), 602 (m), 553 (m), 407 (m). $^1$H-NMR [300 Mhz, DMSO]: $\square$4.01 (2H, d, J=6.2 Hz, CH$_2$), 5.65 (2H, t, J=6.2 Hz, OH) ppm. $^{13}$C-NMR [300 MHz, DMSO]: $\square$28.30, 72.93, 122.03 ppm. UV [MeOH]: $\square_{max}$=202.6 nm.

Example 3

3-(2-propynyloxy)-propane-1,2-diol (4); [13580-38-6]

4 was synthesized from propargyl alkohol 1 and glycidol in DMF. 2-Propyne-1-ol (56.06 g, 1.0 mol) and DMF (0.56 g, 0.01 mol) were heated to 110° C. under stirring. Glycidol (67.30 g, 0.91 mol) was added dropwise within one hour (exotherm reaction!) keeping the temperature in the flask below 150° C. After 3 hours the mixture was cooled to room temperature. The crude product, approx. 95 g of a dark orange oil was distilled in a kugelrohr-distillation apperatus under vacuum and gave 60.2 g of 4 as a slight yellowish oil in 51% yield. BP. 92° C./~1 mbar, n$_D^{20}$=1.4759 (lit. n$_D^{20}$= 1.4761). TLC on silica; EtAc, R$_f$=0.27, The TLC plate needs development in an iodine chamber for visualisation of 4.

Spectroskopic Data

MS [m/z, (% rel. int.), fragment]: 152.8 (100) M+Na. IR [$\square^{KBr}$, cm$^{-1}$]: 3953 (w), 3361 (s, broad, OH), 3293 (s, =C—H), 2933 (m, C—H), 2878 (m, C—H), 2116 (m, C≡C), 1441 (m, CH$_2$), 1360 (m, CO—H), 1269 (m, CH$_2$+ CO—H), 1100 (s, C—O—C), 1037 (s, C—OH), 956 (m), 864 (m), 668 (m), 543 (m). $^1$H-NMR [300 MHz, CDCl$_3$]: $\square$2.51 (1H, t, $^4$J$_{HH}$=2.4 Hz, CH), 3.52–3.74 (6H, m, CH—OH, CH$_2$—OH), 3.86–3.98 (1H, m, CH$_2$—O), 4.20 (2H, d, $^4$J$_{HH}$=2.4 Hz, CH$_2$—O) ppm. $^{13}$C-NMR [300 MHz, CDCl$_3$]: $\square$58.60, 63.80, 70.74, 71.26, 75.04, 79.36 ppm. UV [MeOH]: $\square_{max}$=264.9 nm.

Example 4

3-(2,3-diiodo-2-propenyloxy)-propane-1,2-diol (5)

3-(2-propynyloxy)-propane-1,2-diol (4, 11.73 g, 0.09 mol) was added to a solution of KI (13.28 g, 0.08 mol) and I$_2$ (22.85 g, 0.09 mol) in water (400 ml). The reaction mixture was heated under reflux for 3 hours. The reaction mixture separated into two layers. The lower brown-black organic phase was separated, 28.4 g. The water phase was extracted with diethyl ether (2×100 ml) and the ether phase was evaporated, 4.04 g. The combined organic phases were purified by flash chromatography on silica with ethyl acetate as eluent. 29.2 g of 5 was collected in 84.5% yield. The light yellow oil crystallised in the refrigerator during the night and gave a light yellow solid.

MP. 33–36° C. TLC on silica; EtAc, R$_f$=0.44; MeAc, R$_f$=0.68. Aqueous solubility at 20° C.=18.38 g/L.

Spectroskopic Data

MS [m/z, (% rel. int.), fragment]: 384.0 (0.3) M, 292.9 (76) C$_3$H$_3$I$_2$, 257.0 (26) M-I, 253.9 (17) I$_2$, 183.0 (92) C$_3$H$_4$IO, 130.1 (5) M-2I, 129.1 (13) M-(2I+H), 128.0 (32) M-(2I+2H), 127.0 (21) I, 75.1 (100) C$_3$H$_7$O$_2$. IR [$\square^{KBr}$, cm$^{-1}$]: 4268 (w), 4010 (w) 3409 (s, broad, O—H), 3052 (m, =C—H), 2925 (m, C—H), 2439 (w), 1582 (w), 1440 (m, CH$_2$), 1343 (m, CO—H), 1262 (m, CH$_2$+CO—H), 1221 (s, CO—H), 1126 (s, C—O—C), 1105 (s, C—OH), 1043 (s, C—OH), 1011 (m, C—OH), 977 (m), 934 (m), 850 (m), 782 (s), 702 (m), 639 (m), 542 (m). $^1$H-NMR [300 MHz, DMSO]: $\square$3.25–3.43 (4H, m, CH$_2$—O, CH$_2$—OH), 3.5–3.7 (1H, m, CH—OH), 4.15 (2H, t, $^4$J$_{HH}$=0.8 Hz, CH$_2$—O), 4.53 (1H, t,$^3$J$_{HH}$=5.6 Hz, prim. OH), 4.72 (1H, d, $^3$J$_{HH}$=5.1 Hz, sec. OH), 7.45 (1H, t $^4$J$_{HH}$=0.8 Hz, =CH) ppm. $^{13}$C-NMR [300 MHz, DMSO]: $\square$63.07, 70.29, 71.25, 77.19, 84.71, 101.77 ppm. UV [MeOH]: $\square_{max}$=240.0 nm.

Example 5

3-(2,3,3-triiodo-2-propenyloxy)-propane-1,2-diol (6)

To a stirred solution of 3-(2-propynyloxy)-propane-1,2-diol (4, 13.09 g, 0.1 mol) in H$_2$O (40 ml) at 0° C. was added NaOH (4.04 g, 0.1 mol) and KI (49.81 g, 0.3 mol). 14% aqueous NaOCl (53.01 g, 0.1 mol) was added dropwise over a 1.5 hour period in order to keep the flask temperature between 0 and 10° C. During 30 min a part of 50% aqueous H$_2$SO$_4$ (53.18 g, 0.27 mol) was added dropwise until pH~2, keeping the mixture temperature between 5 an 15° C. The rest of the acid was added simultaneously with 14% aqueous NaOCl (53.01 g, 0.1 mol) during 1.5 hours. The reaction mixture was stirred at room temperature over night. The brown-black lower organic phase (47 g) was separated and the aqueous phase extracted with EtAc (2×50 ml). The EtAc phase was evaporated to dryness, 3 g. The combined organic phases (50 g crude product) crystallized during the night in the refrigerator. The crude product was recrystallized from H$_2$O:EtOH (9:1) and kept at 4° C. over night. The substance precipitated from the solution, was filtered and dried. This gave 38.8 g 6 as a slight yellow cotton like solid in 76% yield. MP. 70–71.5° C. TLC on silica; EtAc, R$_f$=0.48. Aqueous solubility at 20° C.=0.5 g/L.

Spectroskopic Data

MS [m/z, (% rel.int.) fragment]: 435.0 (3) C$_3$H$_2$I$_3$O, 419.1 (32) C$_3$H$_2$I$_3$, 383.2 (25) M-I, 309.1 (91) C$_3$H$_3$I$_2$O, 293.1

(13) C$_3$H$_3$I$_2$, 256.1 (2) M-2I, 255.1 (17) M-(2I+H), 254 (95) I$_2$, 181.1 (9) C$_3$H$_2$IO, 165.1 (100) C$_3$H$_2$I, 129.2 (2) M-3I, 128.0 (23) M-(3I+H), 127.0 (31) I, 75.1 (72) HOCH$_2$CH$_2$OH. IR [$\square^{KBr}$, cm$^{-1}$]: 3365 (m, broad, O—H), 3230 (m, O—H), 2966 (m, C—H), 2901 (m, C—H), 1538 (w), 1464 (m, CH$_2$), 1385 (m, CO—H), 1342 (m, CO—H), 1269 (m, CH$_2$+CO—H), 1245 (m, CH$_2$+CO—H), 1218 (w), 1121 (s, C—O—C), 1082 (s, C—OH), 1066 (s, C—OH), 1024 (m, C—OH), 981 (m), 936 (m), 895 (m), 840 (m), 731 (m), 706 (m), 608 (m), 529 (m), 486 (m), 419 (w). $^1$H-NMR [300 MHz, DMSO]: $\square$3.24–3.44 (4H, m, CH$_2$—O, CH$_2$—OH), 3.54–3.64 (1H, m, CH—OH), 4.12 (2H, s, CH$_2$—O), 4.50 (1H, t, $^3$J$_{HH}$=5.7 Hz, prim. OH), 4.69 (1H, d, $^3$J$_{HH}$=5.2 Hz, sec. OH) ppm. $^{13}$C-NMR [300 MHz, DMSO]: $\square$23.41, 63.08, 70.32, 71.23, 80.83, 116.83 ppm.

Eksempel 6

2,2'-[2,3-diiodo-2-butene-1,4-diylbis(oxy)]-bis-etanol (9)

1,4-bis-(2-hydroxyethoxy)-2-butyne (8, 87.12 g, 0.50 mol) was added to a solution of KI (172.04 g, 1.04 mol) and I$_2$ (129.51 g, 0.51 mol) in water (1500 ml). The reaction mixture was heated under reflux for 3 hours and stirred at roomtemperature over night. The lower brown-black organic phase was separated and the aqueous phase was extracted with diethyl ether. The combined organic phases were evaporated and gave 289 g crude product. 7 g of the crude product were purified by preperative HPLC (RP-18 column with H$_2$O:CH$_3$CN=8:2). This gave 1.7 g of 9 as a slight yellow cotton like solid in 24% yield. MP. 79–82° C. TLC on silica; EtAc:CH$_3$CN=1:1, R$_f$=0.52. Aqueous solubility at 20° C.=7.2 g/L.
Spectroskopic Data
MS [m/z, (% rel.int.) fragment]: 451 (100) M+Na, 429 (8) M+H. IR ($\square^{KBr}$, cm$^{-1}$): 3306 (m, broad, O—H), 3204 (m, bred, O—H), 2932 (m, C—H), 2862 (m, C—OH), 1497 (w), 1435 (m, CH$_2$), 1344 (m, CO—H), 1285 (w), 1266 (m, CH$_2$+CO—H), 1208 (m, CO—H), 1119 (s, C—O—C), 1057 (s, C—OH), 996 (m, C—OH), 902 (s, C—OH), 831 (m), 666 (m), 533 (w), 484 (m). $^1$H-NMR [300 MHz, DMSO]: $\square$3.38–3.58 (8H, m, CH$_2$—CH$_2$—OH), 4.37 (4H, s, CH$_2$—O), 4.64 (2H, t, $^3$J$_{HH}$=5.5 Hz, OH) ppm. $^{13}$C-NMR [300 MHz, DMSO]: $\square$59.93, 70.92, 81.68, 103.32 ppm.

Example 7

3-[(4-Hydroxy-2-butynyl)oxy]-propane-1,2-diol (10); [81748-55-2]

At room temperature glycidol (23.28 g, 0.317 mol) was added to 2-butyne-1,4-diol (7, 18.11 g, 0.21 mol) and stirred until the mixture became homogeneous. A solution of CaCl$_2$ (35.18 g, 0.317 mol) in H$_2$O (65 ml) was added. The reaction was exotherm and the mixture turned yellow and more viscous. After the generation of heat stopped the reaction mixture was stirred at 50° C. for 6 hours. TLC on silica; EtAc:EtOH=9:1, (10) R$_f$=0.24, (7) R$_f$=0.46. The mixture was used directly in the following iodination reaction to (13), see example 10.

Example 8

3,3'-[2-butyne-1,4-diylbis(oxy)]-bis-propane-1,2-diol (11); [81748-56-3]

At room temperature glycidol (32.52 g, 0.44 mol) was added to 2-butyne-1,4-diol (7, 18.11 g, 0.21 mol) and stirred until the mixture became homogeneous. LiOH (0.024 g, 0.001 mol) was added and the reaction mixture was stirred at 50° C. for 6 hours. TLC on silica; EtAc:EtOH=9:1, (11) R$_f$=0.11, (10) R$_f$=0.24, (7) R$_f$=0.46. The mixture was used directly in the following iodination reaction to (14), see example 11.

Example 9

2,3-diiodo-2-butene-1,4-diol (12); [19095-64-8] & [62994-00-7]

12 was synthesized from 2-butyne-1,4-diol (7) as described by Iserson, H., Smith, H. Q., U.S. Pat. No. 3,342,582, Sep. 19, 1967. The crude product was recrystallized from water and gave 12 in 93% yield. MP. 179.5–180.5° C. (lit. 179–180° C.). TLC on silica; EtAc:CH$_3$CN=1:1, R$_f$=0.70; EtAc:EtOH=9:1, R$_f$=0.67. Aqueous solubility at 20° C.=0.534 g/L.
Spectroskopic Data
MS [m/z, (% rel. int.), fragment]: 340.1 (97) M, 253.9 (7) I$_2$, 195 (100) M-(H$_2$O+I), 127.0 (19) I, 86.1 (93) M-2I, 68.1 (40) M-(H$_2$O+2I). IR [$\square^{KBr}$, cm$^{-1}$]: 3212 (s, broad, O—H), 2932 (m, C—H), 2919 (m, C—H), 2863 (m, C—H), 2826 (m, C—H), 2639 (w), 2560 (w), 2448 (w), 2089 (w), 2022 (w), 1448 (m, CH$_2$), 1419 (m, CH$_2$), 1350 (m, CO—H), 1231 (m, CH$_2$+CO—H), 1075 (s, C—OH), 1069 (s, C—OH), 1010 (s, C—OH), 999 (s, C—OH), 755 (m), 609 (m), 526 (m). $^1$H-NMR [300 MHz, DMF]: $\square$4.36 (4H, s, CH$_2$), 5.60 (2H, s, OH) ppm. $^{13}$C-NMR [300 MHz, DMF]: $\square$75.22, 105.10 ppm. UV [MeOH]: $\square_{max}$=238.8 nm.

Example 10

3-[(2,3-diiodo-4-hydroxy-2-butenyl)oxy]-propane-1,2-diol (13)

The reaction mixture of 10 (0.21 mol) from example 7 was added to a solution of KI (70.20 g, 0.423 mol) and I$_2$ (53.55 g, 0.211 mol) in H$_2$O (550 ml). The mixture was heated under reflux for 3.5 hours. 20% aqueous Na$_2$S$_2$O$_5$ was added to the dark reaction mixture until no further reduction in color was observed (total added 15 ml). The light yellow suspension was filtered to remove precipitated 12 and the filtrate was concentrated to half the volume. The aqueous phase was extracted with MeAc (5×250 ml). The MeAc fractions were collected, filtered and evaporated to dryness. The residue was again extracted with MeAc (5×250 ml). ). The MeAc fractions were collected, filtered and evaporated to dryness. This gave 21.4 g crude product. 15.6 g crude product were purified by chromatography on silica with gradient elution starting with EtAc and ending with EtAc:MeOH=9:1. This gave 7.39 g (13) as a light brown, viscous oil. n$_{D18}$=1.638. TLC on silica; EtAc:EtOH=9:1, R$_f$=0.44. Aqueous solubility at 20° C. is greater than 1.2 g/L.
Spectroskopic Data
MS [m/z, (% rel.int.) fragant]: 437 (100) M+Na. IR ($\square^{KBr}$, cm$^{-1}$): 3386 (s, broad, O—H), 2911 (m, C—H), 2870 (m, C—H), 1710 (w), 1626 (w), 1442 (m, CH$_2$), 1351 (m, CO—H), 1235 (m, CH$_2$+CO—H), 1110 (s, C—O—C), 1056 (s, C—OH), 955 (m), 927 (m), 865 (m). $^1$H-NMR [300 MHz, DMSO]: $\square$3.24–3.46 (4H, m, CH$_2$—O), 3.56–3.66 (1H, m, CH—O), 4.22 (2H, d, $^3$J$_{HH}$=6.0 Hz, CH$_2$—C=), 4.35 (2H, s, CH$_2$—C=), 4.49 (1H, S, $^3$J$_{HH}$=5.6 Hz, prim. OH), 4.68 (1H, S, $^3$J$_{HH}$=5.1 Hz, sec. OH), 5.59 (1H, t, $^3$J$_{HH}$=6.0 Hz, prim. OH) ppm. $^{13}$C-NMR [300 MHz, DMSO]: $\square$63.15, 70.36, 71.22, 73.70, 82.07, 99.44, 108.77 ppm.

Example 11

3,3'-[2,3-diiodo-2-butene-1,4-diylbis(oxy)]-bis-propane-1,2-diol (14)

The reaction mixture of 11 (0.21 mol) from example 8 was added to a solution of KI (69.45 g, 0.42 mol) and I$_2$ (53.06 g, 0.21 mol) in H$_2$O (645 ml). The mixture was heated under reflux for 3.5 hours. 20% aqueous Na$_2$S$_2$O$_5$ was added to the dark reaction mixture until no further reduction in color was observed (total added 20 ml). The light yellow suspension was filtered to remove precipitated 12 and the filtrate was evaporated to dryness. The residue was resuspended in MeOH (400 ml). Insoluble inorganic salts were filtered and the filtrate was evaporated to dryness, yielding ca. 180 g crude product. A minor part of the crude product was purified by preparative HPLC (RP-18 column with H$_2$O:CH$_3$CN=9:1). This gave 1.3 g 14 as a light yellow cotton like solid. MP. 80.5–82.5° C. TLC on silica; EtAc:EtOH=9:1, R$_f$=0.25. Aqueous solubility at 20° C. is greater than 1.2 g/L.

Spectroskopic Data

IR ($\square^{KBr}$, cm$^{-1}$): 3355 (s, broad, O—H), 2898 (m, C—H), 2866 (m, C—H), 1448 (m, CH$_2$), 1347 (m, CO—H), 1246 (m, CH$_2$+CO—H), 1125 (s, C—O—C), 1051 (s, C—OH), 1009 (s, C—OH), 928 (m), 850 (w), 827 (w), 665 (w), 611 (w), 568 (w), 533 (m). $^1$H-NMR [300 MHz, DMSO]: $\square$3.27–3.44 (8H, m, CH$_2$—O), 3.56–3.66 (2H, m, CH—O), 4.37 (4H, s, CH$_2$—C≡), 4.49 (2H, t, $^3$J$_{HH}$=5.6 Hz, prim. OH), 4.67 (2H, d, $^3$J$_{HH}$=5.6 Hz, sec. OH) ppm. $^{13}$C-NMR [300 MHz, DMSO]: $\square$63.10, 70.34, 71.27, 81.94, 103.17 ppm.

Example 12

2,3,4,5-tetraiodo-2,4-hexadiene-1,6-diol (16); [13231-82-8]

16 was synthesized from 2,4-hexadiyne-1,6-diol (15) as described by Iserson, H., Smith, H. Q., U.S. Pat. No. 3,342,582, Sep. 19, 1967, but the workup was done in a different way. The crude product was purified by flash chromatography on silica with EtAc as eluent and recrystallized from i-PrOH/H$_2$O (1:2). This gave 16 as orange crystals in 43% yield. MP. 94–96° C. (lit. 95–96° C.). TLC on silica; EtAc:CH$_3$CN=1:1; R$_f$=0.73. Aqueous solubility at 20° C.=0.183 g/L.

Spectroskopic Data

MS [m/z, (% rel. int.), fragment]: 490.8 (30) M-I, 363.9 (25) M-2I, 253.8 (100) I$_2$, 237.0 (5) M-3I, 127.0 (41) I, 110.9 (20) M-4I. IR [$\square^{KBr}$, cm$^{-1}$]: 4360 (w), (m, OH), 3258 (s, broad, OH), 2917 (m, C—H), 869 (m, C—H), 2682 (w), 1684 (w, conj. C=C), 1623 (w, conj. C=C), 1560 (w), 1528 (w), 1426 (m, CH$_2$), 1354 (m, CO—H), 1233 (m, CH$_2$+CO—H), 1055 (s, C—OH), 1027 (s, C—OH), 998 (m), 963 (m), 936 (m), 700 (m), 650 (m), 590 (m), 562 (m). $^1$H-NMR [300 MHz, DMSO]: $\square$4.09 (4H, s, CH$_2$), 5.66 (2H, s, OH) ppm. $^{13}$C-NMR [300 MHz, DMSO]: $\square$72.18, 103.05, 110.54 ppm.

Example 13

3-[6-(2,3-Dihydroxy-propoxy)-hexa-2,4-diynyloxy]-propane-1,2-diol (17)

An aqueous NH$_4$Cl solution was saturated at 5° C. CuCl (1.0 g, 18.7 mmol) was added to 20 ml of the saturated aqueous NH$_4$Cl solution. The reaction vessel was filled with O$_2$ and the mixture was vigorously stirred during the whole reaction time. 3-(2-propynyloxy)-propane-1,2-diol (4, 13.01 g, 100 mmol) was added at room temperature in 5 portions during 2.5 hours. The reaction mixture was stirred at 40° for 1 hour and then evaporated to dryness. The residue was dissolved in 50 ml CH$_3$CN:H$_2$O=1:1 and filtered through 20 g silica 60. The filter column was washed with 100 ml CH$_3$CN:H$_2$O=1:1 and the filtrate was evaporated to dryness.

The residue was suspended in MeOH (70 ml) and insoluble inorganic components removed by filtration. The filtrate was diluted with water (500 ml) and stirred with ion exchangers (IRA 67, 110 ml; AMB 200 C, 110 ml) and activated carbon (0.1 g). The ion exchangers were filtered off and washed with water (2×250 ml). The combined filtrates were evaporated and gave 9.8 g 17 as a light yellow oil in 76% yield. TLC on silica; H$_2$O:CH$_3$CN=1:1, R$_f$=0.79; CH$_3$CN, R$_f$=0.26.

Spectroskopic Data

MS [m/z, (% rel. int.), fragment]: 259 (6) M+H, 167 (100) M-[CH$_2$—O—CH$_2$—CH(OH)—CH$_2$OH]. IR [$\square^{KBr}$, cm$^{-1}$]: 3381 (s, broad, OH), 2934 (m, C—H), 2880 (m, C—H), 2115 (w, C≡C), 1401 (m, CH$_2$), 1352 (m, CO—H), 1263 (m, CH$_2$+CO—H), 1089 (s, C—O—C), 1035 (s, C—OH), 950 (m), 864 (m), 673 (m), 556 (m). $^1$H-NMR [300 MHz, DMSO]: $\square$3.30–3.50 (8H, m, CH$_2$—O), 3.56–3.62 (2H, m, CH—O), 4.20 (4H, s, CH$_2$—O), 4.52 (2H, t, prim. OH), 4.72 (2H, d, sec. OH) ppm. $^{13}$C-NMR [300 MHz, DMSO]: $\square$58.12, 62.83, 69.38, 71.75, 76.65 ppm.

Example 14

3-[6-(2,3-Dihydroxy-propoxy)-2,3,4,5-tetraiodo-hexa-2,4-dienyloxy]-propane-1,2-diol (18)

The reaction mixture of 17 (8.0 g, 31 mmol) from example 13 was added to a solution of KI (20.57 g, 0.123 mol) and I$_2$ (15.72 g, 62 mmol) in H$_2$O (300 ml). The mixture was heated to 70° C. for 2 hours and was stirred over night at room temperature. 37% aqueous NaHSO$_3$ was added to the dark reaction mixture until no further reduction in color was observed (total added 40 ml). The reaction mixture was evaporated to dryness. The residue was suspended in MeOH (150 ml). Insoluble inorganic salts were filtered off and the filtrate was evaporated to dryness, yielding ca. 40 g crude product. The residue was suspended in EtOH (200 ml). Insoluble inorganic salts were filtered off and the filtrate was evaporated to dryness, yielding ca. 30 g crude product. TLC on silica; CH$_3$CN, R$_f$=0.62.

The crude product was purified by preparative HPLC (RP-18 column with H$_2$O:CH$_3$CN=9:1).

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method for the generation of an X-ray contrast image of a human being or an animal subject comprising administering an effective amount of a compound having the formula A:

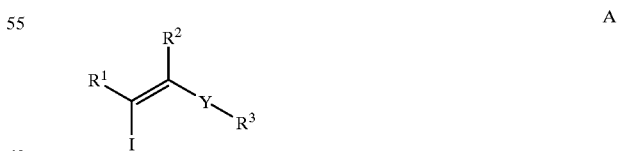

A wherein
Y is (IC=CI)$_{0-1}$ and R$^1$ and R$^2$ are each iodine or an electronically neutral group (C-group) and R$^3$ is a C-group, to the subject and generating an X-ray image.

2. The method of claim 1 wherein the subject is a human being.

3. The method of claim 1 wherein $R^3$ has an area for resonance effect R of a magnitude between 0.06 and −0.45, and a field inductive effect F between 0.24 and −0.03.

4. The method of claim 1 wherein $Y=(IC{=}CI)_{0-1}$ $R^1$=H, I, $CH_2OH$, $R^3$ $R^2$=H, I, $CH_2OH$, $R^3$ $R^3$=H, $CH_2$—$R^4$, $CH_2$—$R^5$, $CH(R^4)_2$, $CHR^4R^5$, $R^5$ $R^4$=O—$R^5$, O—$(CH_2CH_2$—$O)_{1-7}$—$R^6$, NH—CO—$R^6$, NH—CO—O—$R^6$, O—CO—$R^6$, O—CO—NH—$R^6$ $R^5$=H, $C_{1-7}$ alkyl chain which is unbranched or branched and which is substituted with one or several OH-groups.

$R^6$=H, $C_{1-6}$ alkyl chain, $R^5$.

5. A compound having the following formula:

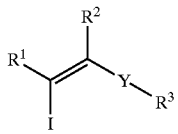

A wherein $Y=(IC{=}CI)_{0-1}$;

$R^1$=H, I, $CH_2OH$, $R^3$;

$R^2$=H, I, $R^3$;

$R^3$=$CH_2$—$R^4$, $CH_2$—$R^5$, $CH(R^4)_2$, $CHR^4R^5$, $CR^4(R^5)_2$, $R^5$;

$R^4$=O—$R^5$, NH—CO—$NH_2$;

$R^5$=$C_{3-8}$ alkyl chain which is unbranched or branched and which is substituted with two or more OH-groups.

6. The compound of claim 5 having the formula 3-[6-(2,3-Dihydroxy-propoxy)-2,3,4,5-tetraiodo-hexa-2,4-dienyloxy]-propane-1,2-diol.

7. The compound of claim 5 having the formula 3,3'-[2,3-diiodo-2-butene-1,4-diylbis(oxy)]-bis-propane-1,2-diol.

8. The compound of claim 5 having the formula 3-[(2,3-diiodo-4-hydroxy-2-butenyl)oxy)]-propane-1,2-diol.

9. A composition comprising the compound of claim 5 admixed with at least one physiological carrier or solvent.

* * * * *